United States Patent [19]

Negishi et al.

[11] Patent Number: 4,894,777
[45] Date of Patent: Jan. 16, 1990

[54] OPERATOR MENTAL CONDITION DETECTOR

[75] Inventors: Hirokazu Negishi, Epsom Survey, United Kingdom; Masao Hosaka, Sagamihara, Japan

[73] Assignee: Canon Kabushiki Kaisha, Tokyo, Japan

[21] Appl. No.: 78,647

[22] Filed: Jul. 28, 1987

[30] Foreign Application Priority Data

Jul. 28, 1986 [JP] Japan ............................. 61-175718

[51] Int. Cl.$^4$ .................................................. A61B 5/00
[52] U.S. Cl. ............................... 364/419; 364/188; 364/413.02; 128/734; 128/905; 434/236
[58] Field of Search ............... 364/413, 415, 419, 188, 364/413.02; 128/733, 734, 745, 670, 905; 434/236

[56] References Cited

U.S. PATENT DOCUMENTS

| | | | |
|---|---|---|---|
| 4,312,358 | 1/1982 | Barney | 128/670 |
| 4,464,121 | 8/1984 | Perelli | 434/236 |
| 4,683,891 | 8/1987 | Cornellier et al. | 128/734 X |
| 4,725,824 | 2/1988 | Yoshioka | 128/733 X |
| 4,751,642 | 6/1988 | Silva et al. | 364/413 |

Primary Examiner—Allen MacDonald
Attorney, Agent, or Firm—Fitzpatrick, Cella, Harper & Scinto

[57] ABSTRACT

An information processing apparatus includes a processor for performing various information processing operations in accordance with an instruction from an operator, a bioinformation sensor for detecting a mental condition of the operator, and an output unit for outputting corresponding information to the operator based on the detected mental condition. The operator is relaxed by the information output from the output unit.

65 Claims, 4 Drawing Sheets

OPERATOR MENTAL CONDITION DETECTOR

BACKGROUND OF THE INVENTION

1. Field of the Invention

The present invention relates to an information processing apparatus.

2. Related Background Art

In recent years, office automation equipment (to be referred to as OA equipment hereinafter) has been used in various application fields, and its importance has increased. Along with the "Second Industrial Revolution", the importance of an MMI (Man-Machine Interface) is recognized, and the need therefore has increasingly arisen.

The MMI results from considering how a machine looks from man's view point, and hence aims at a user friendly system.

However, the Second Industrial Revolution is an innovation centering around the computer replacing some functions performed by man's brain, in particular, a microcomputer comprising a high-performance semiconductor computer. In a sense, a machine is superior to man in performing some functions, and in the present state of the MMI, the intelligent machine is difficult for man to use.

In the early days of the First Industrial Revolution machines performed labor previously performed by man and brought about an alienation of man from machine. Charlie Chaplin's "MODERN TIMES" cynically satirized this alienation. There is therefore a need for a human MMI in order to avoid a second "MODERN TIMES".

The intelligent machine represented by a microcomputer causes greater alienation of man than that caused by the First Industrial Revolution. The present innovation centering around the computer developed from the use of computers in a computer room where only specialists used the computer, into OA, FA (factory automation), and HA (home automation) and has spread from the factory to the home. However, on the whole, this development is merely the leading wave of a much larger wave of new developments in computer technology. When emotionally maladjusted individuals use intelligent machines, the sense of alienation normally experienced can develop into stress or neurosis. At present, a Third Industrial Revolution is arising due to the development of the fifth generation computer.

For example, in recent information processing apparatuses, an icon displayed on a screen is moved by a mouse (a coordinate input devices) to select a desired menu or processing. Thus, recent information processing apparatuses tend to be easy to use.

However, since the keyboard and mouse must be selectively used, the mouse and icon are intermediary constructs through which the machine and man communicate. Machine and man do not communicate directly. Recent information processing apparatus have not yet reached the level at which man communicates directly with man.

Another problem is caused by the fact that man is managed by machines. To make the machine user friendly or to develop a cyborg or a high-performance robot is the ultimate object. in producing machines capable of efficient interaction with man Personification of the operation of various information equipment is a large step in achieving this goal. However, at present, almost no study or development is being in this area.

SUMMARY OF THE INVENTION

It is an object of the present invention to provide an information processing apparatus with which an MMI is improved to become a PMI (Personalized Machine Interface) by introducing a friendly character such as a second generation icon to information equipment, software, and the like, on the basis of the psychological inclinations of man.

Note that the PMI aims at improving the MMI, and personalization has both the meanings of personification and individualism.

It is therefore another object of the present invention to provide an information processing apparatus satisfying at least one of the following conditions:

(1) a user is individually identified to automatically select an MMI suitable for him or her;

(2) skill correspondence:

the apparatus interacts with the user according to the user's total access time, frequency of use, preferences, and actual results;

(3) PMI monitor:

the apparatus must comprise hardware and an OS capable of realizing the above items;

(4) hardware must be constituted by means for achieving the PMI and means for controlling equipment, and must be implemented within an appropriate cost range;

(5) the apparatus need only have an information volume sufficient to induce an association on the the part of the user between the output of the apparatus and tasks or behavior the user is to perform since the apparatus appeals to the psychology of the user. Therefore, the display need not always be a high-quality and full-color image and a small icon-like character of a line image need only be displayed; and (6) the apparatus must appeal to the psychology of the user to cause a user to understand and respond to the status of equipment, the type of operation, a self failure diagnosis, and commands while personificating a machine without applying a heavy load to the equipment.

It is still another object of the present invention to eliminate the conventional drawbacks in consideration of the above situation.

It is still another object of the present invention to provide an apparatus for causing detection means to detect a mental condition of an operator and for causing output means to output information based on the detected mental condition.

It is still another object of the present invention to provide an apparatus for causing selection means to select basic information of an operator from those corresponding to a plurality of different operators stored in storage means and for causing output means to output information corresponding to a mental condition of the operator detected by detection means based on the selected basic information.

DETAILED DESCRIPTION OF THE PREFERRED EMBODIMENT

An embodiment according to the present invention will now be described with reference to the accompanying drawings. The characteristic feature of the present invention may be achieved by a single piece of equipment or by a system consisting of a plurality of pieces of equipment.

At present, a speech input apparatus is proposed as a simple MMI method and device. However, even this apparatus can only release a user from a cumbersome key input operation; it is not an ultimate MMI means. In particular, it is difficult for current techniques to realize speech recognition of a plurality of users.

As the characteristic feature of the present invention, the psychological inclination of an operator is sensed by a machine, and the communication is requested from the machine to man.

For this purpose, a method and apparatus are proposed wherein access to a machine or a rest state of an operator is detected by the machine by the operator responding to speech from the machine or by the machine discriminating whether or not the operator wishes to use the machine. The machine waits for a set-up (e.g. power-on or initialization), and a speech recognition function is actuated to permit the machine to communicate with an operator by means of speech. However, this method is no better than the MMI, and simplifies the interface with the machine. The PMI cannot be realized unless the machine accesses the mental condition of the operator.

In this embodiment, the information processing apparatus is applied to a PC (personal coumputer) or a WP (word processor). However, the present invention is not limited to this but can be applied to the equivalent relationship between an NC machine, large-scale equipment, and the like, with an operator.

An operator normally operates a keyboard while watching a CRT (display apparatus), and the machine executes various processing operations in accordance with key data or data stored in a memory based on data or an instruction inputted from the keyboard. However, how does the machine sense the mental condition of the operator?

In a first method, data indicating personality, blood type, and the like of an operator is input beforehand to the machine together with a self ID. No. (identification number). In a second method, the mental condition of the operator can be checked based on the pupil movement of the operator, body temperature, room temperature, pulsation, blood pressure, and input errors sensed by a sensor of the machine. This is done only to sense ordinary events. However, with this method, the machine can grasp the personality and the mental condition of the operator, and may display a message on a screen or announce a message by voice as if it were a good friend. Note that the above data can also be detected by monitoring the access time of the operator.

Figure 1:
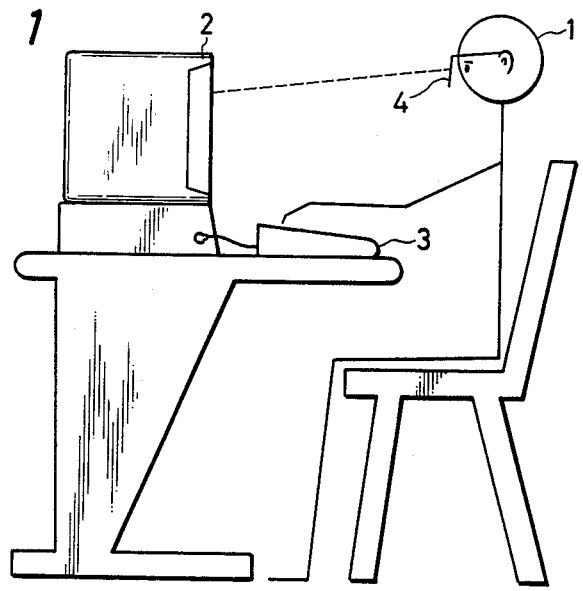
FIG. 1 is a view showing a state wherein an operator uses an information processing apparatus of this embodiment.
Figure 2:
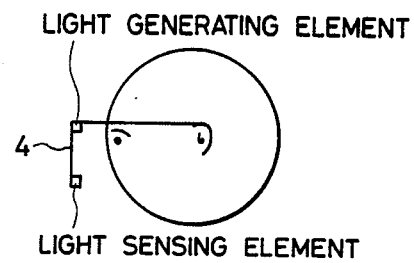
FIG. 2 is a view showing a state wherein an operator wears OA spectacles.

FIG. 1 shows a detection example of bioinformation. FIG. 1 shows a state wherein an operator 1 operates OA equipment (e.g., a word processor).

In this state, the mental condition of the operator 1 is detected as described above. First, OA spectacles 4 will be described.

Figure 3:
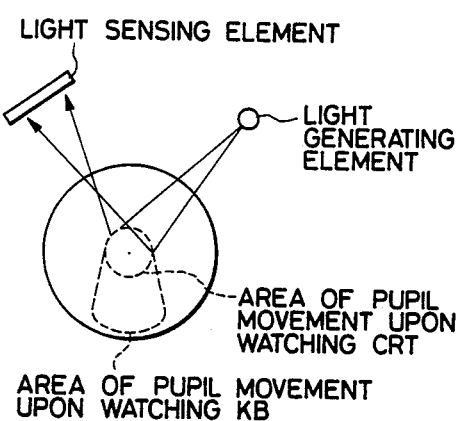
FIG. 3 is a view showing a pupil movement range detected by the OA spectacles.
Figure 4:
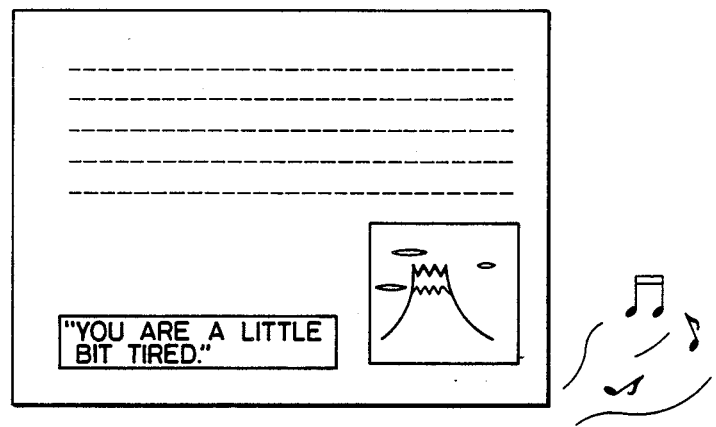
FIG. 4 illustrates an example of output information of this embodiment.

The OA spectacles 4 have a far-infrared sensor capable of continuously tracing the pupil movement of the operator 1. In practice, a light generating element for generating a weak far-infrared beam is arranged at one end of the OA spectacles 4, and transmit the beam toward the pupil. Since the operator's pupil is blackish, no light reflected thereby is obtained (or light is attenuated). When the beam falls outside the pupil, light reflected thereby is received by a light sensing element. The directivity of the light generating element can be adjusted so that no light reflected by the pupil is obtained when the pupil is moved within the area in which the operator watches the screen of a display apparatus 2. Note that in FIG. 3, an area of pupil movement upon watching a keyboard 3 and an area of pupil movement upon watching the CRT can be identified. When the pupil is out of this area or frequently out of the area, it is discriminted that the degree of fatigue of the operator 1 becomes considerable or that the operator cannot concentrate himself or herself on the operation, and a message "Short Break?" or an image that an operator likes or prefers is displayed on a portion of the screen. FIG. 4 shows this state. In FIG. 4, a landscape that the operator likes is displayed on a portion of the screen, and at the same time, an operator's favorite BGM (background music) can be reproduced. Therefore, since different individuals prefer the displayed image or the BGM, a self ID. No. must be input to the apparatus before the apparatus is started. Thus, the apparatus can discriminate the mental condition of the operator based on data corresponding to the input ID. No. with high precision.

Means for detecting the mental condition of the operator is not limited to the OA spectacles described above. For example, as has been described above, the mental condition of the operator can be detected based on an environment condition when the operator uses the apparatus and on the body temperature, pulsation, blood pressure, and input errors of the operator. For this purpose, a temperature sensor, a pulsation sensor, a blood pressure sensor, and a sensor for detecting depression pressure are arranged in some keys of the keyboard 3 (a carriage return key and a space key which are frequently used are preferable) to detect a change in mental condition. The keyboard 3 having the above function can detect that a depression pressure depressing the keyboard 3 becomes higher than an ordinary pressure or can count the number of correction errors upon depression of wrong keys. The apparatus can communicate with the operator in accordance with the frequency while the realizing a man-machine interaction.

Information indicating the mental condition of the operator such as changes in pupil movement, input error frequency, pulsation, body temperature, blood pressure, and the like is sensed by the apparatus, and the apparatus learns when the user experiences a degree of fatigue, so that communication depending on the detection state can be performed.

Figure 5:
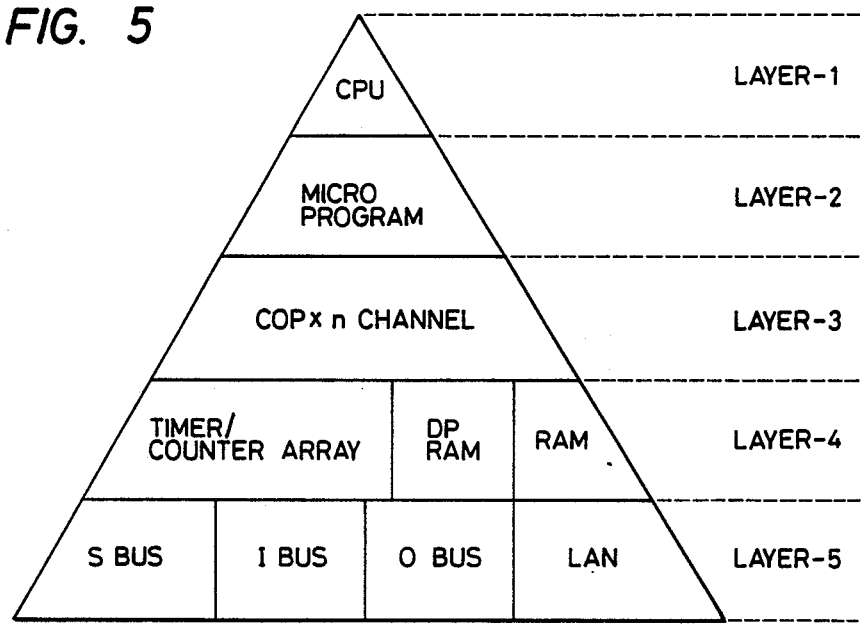
FIG. 5 is a view showing architecture of a controller constituting the information processing apparatus of this embodiment.

FIG. 5 shows the architecture of a controller constituting OA equipment according to the present invention. Along with the recent development of semiconductor process techniques, the controller can be formed on a single chip. As the feature of FIG. 5, a plurality of channels of co-processors (COP) for controlling an actual task are provided to a single chip as needed in addition to a CPU. Therefore, the CPU need only execute the OS (operating system) for managing the COPs. As in this embodiment, the fact that the machine has a function for detecting and learning the mental condition of the operator means that the machines has AI (artificial intelligenece). Therefore, a plurality of processors capable of high-speed parallel processing are preferably arranged.

In FIG. 5, layer-2 incorporates a microprogram allowing high-speed operation of the CPU. This program is adopted to execute at high speed a complicated program used for understanding an operator upon interaction with the operator.

Layer-3 includes a COP group. Processors of channel 0 to channel 16 can be independently parallel-operated. These processors are not directly related to the scope of the present invention, and a detailed description thereof is omitted.

Layer-4 includes a timer/counter array which can be accessed by the CPU and the COPs. Note that each COP incorporates 14 channels of timer/counters. A DPRAM (dual port RAM) is used for data exchange between the CPU and the COP and between the COPs. A RAM (2 clutch band RAM) can be accessed by the COPs and CPU. Layer-5 includes a bus line used for an interface with an external circuit (outside the controller). An S bus is used for expansion of an external memory and I/O ports.

An I bus is specially used for an ICE. Upon debugging of the system, the content of a register RAM (not shown) can be extracted through this bus, and can be checked.

An O bus is an I/O bus, and can be used for expansion for an I/O element.

In a serial I/O interface LAN, a predetermined protocol is constituted by a program, and the COPs are assigned thereto to perform serial communication.

Figure 6:
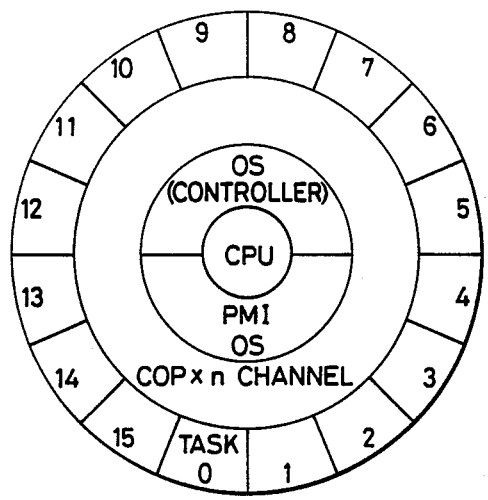
FIG. 6 is a view showing the relationship between tasks and an operating system.

FIG. 6 shows tasks for realizing the information processing apparatus of this embodiment and layers of the OS. As described above, in this embodiment, a plurality of COPs which can be parallel-executed are arranged around the CPU, and some COPs can be assigned to PMI control. This OS includes a normal machine control OS and a PMI OS. The PMI OS can be considered as an OS having an AI-like function for gradually learning the habits or personality of an operator through an interaction with the operator and for allowing better understanding. The COPs are arranged around the PMI OS, and parallel-execute corresponding tasks 0 to 15.

Assignment of the PMI tasks 0 to 15 can be determined depending on the software architecture. The number of COPs can be increased or decreased in accordance with one's work load.

In order to execute the above-mentioned processing, a special OS is required. In order to execute the AI-like PMI-OS having a learning function, high-speed parallel-processing processors are necessary. The architecture of this embodiment is suitable for these OS and processors.

Figure 7:
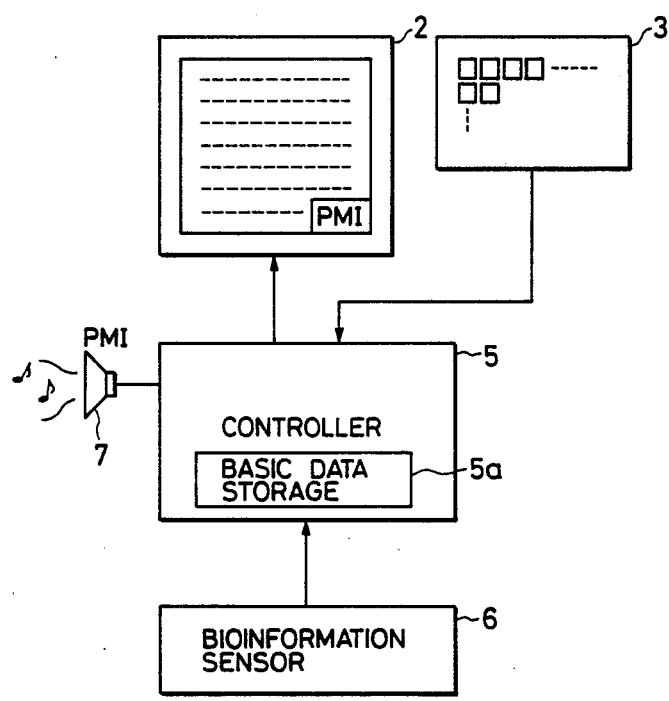
FIG. 7 is a view showing a basic arrangement of the information processing apparatus of this embodiment.

FIG. 7 shows an arrangement when this system is applied to OA equipment. For the PMI arrangement, a bioinformation sensor 6, a display 2 for performing a PMI display on a portion of its screen, and a loudspeaker 7 for aural alarming, are arranged. A controller 5 controls the entire apparatus, and comprises a basic data storage 5a for storing basic data (data indicating personality and favor) for each operator.

With this arrangement, the low-cost PMI of a higher level than a conventional MMI can be easily realized.

Figure 8:
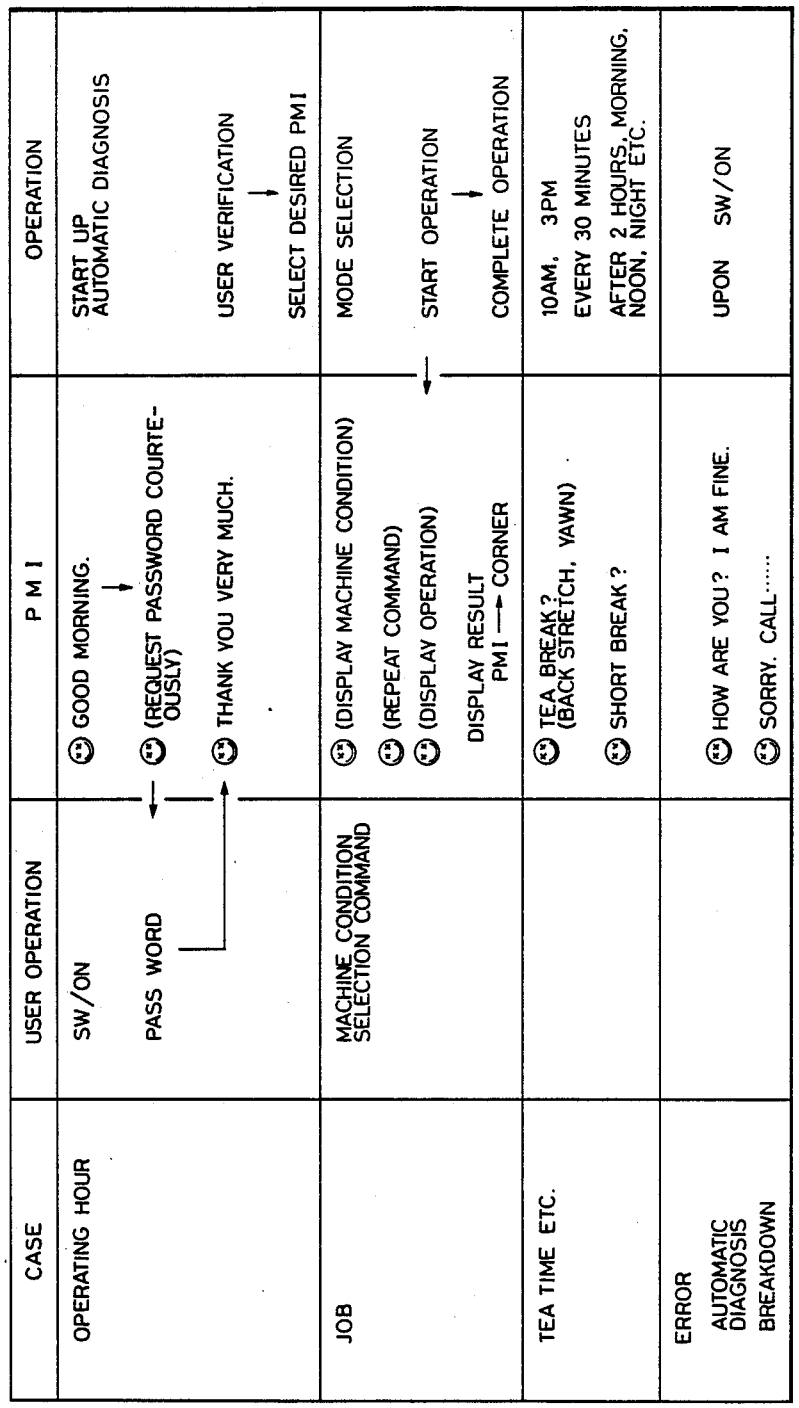
FIG. 8 is a table showing operating states which are changed over time according to this embodiment.

FIG. 8 shows messages and announcements of the PMI in accordance with the lapse of time in this embodiment. When the OA equipment is turned on, "Good Morning: is first displayed or announced. Since the equipment is not always turned on in the morning, greeting data corresponding to turn-on time may be output. If necessary, a password or an ID. No. is input. When the ID. No. is input, the apparatus can identify the operator. Therefore, when the following mental condition is detected to output a message, output data best suitable for the operator is output. For example, in FIG. 8, a message "Tea Break?" (at 10 (AM) and 3 (PM)) is displayed. If the operator is fond of coffee, a message can be modified like "Coffee Break?". Since an image output at this time varies depending on the personal preferences or differences, the image displayed on the display is not always the same. For example, images of a mountain, a sea, a popular singer, an idol, a Buddha, and the like can be output depending on the preferences of the operator. In addition, sounds such as classic music, popular songs, bird's songs, rippling waves, and the like can also be output. Therefore, an image and sound that can confort the operator can be output. Therefore, the input of the ID. No. is necessary for the device to select personal basic data prestored in the apparatus, and the content of the output messages can be modified as needed. Of course, if no ID. No. is used, general output data can be output.

According to this embodiment, the machine and man can understand each other, an operator does not suffer from mental diseases such as neurosis due to alienation from the device, and interaction with the machine can be smoothly performed.

Since the machine detects the bioinformation, and accesses information for the operator, a good relationship between the operator and the machine can be assured, and the machine can make an announcement corresponding to a condition at that time to eliminate errors.

If the apparatus prestores personal basic data of operators, a still appropriate message output can be made.

What is claimed is:

1. An information apparatus comprising:
   processing means for performing various information processing operations in accordance with an instruction from an operator;
   detection means for detecting a mental condition of the operator by detecting information indicating the personality of the operator during the information processing operations performed by said processing means in accordance with an instruction from the operator; and
   output means for outputting information corresponding to the detected mental condition of the operator for relaxing the operator.

2. An apparatus according to claim 1, wherein said output means comprises acoustic output means for outputting a speech message or a melody.

3. An apparatus according to claim 1, wherein said output means outputs image information.

4. An apparatus according to claim 1, wherein said output means comprises means for generating a message representing an inquiry to the operator.

5. An apparatus according to claim 1, wherein said output means comprises means for generating variable sound information in response to the mental condition of the operator.

6. An apparatus according to claim 1, further comprising:
   means for determining the time;
   power detecting means for detecting that said apparatus is supplied with power; and
   means for controlling said output means to output a timely message to the operator in response to the time determined by said determining means when said power detecting means detects that said apparatus is supplied with power.

7. An information apparatus comprising:
   processing means for performing various information processing operations in accordance with an instruction from an operator;
   detection means for detecting a mental condition of the operator during the information processing operations performed by said processing means in accordance with an instruction from the operator; and
   output means for outputting information corresponding to the detected mental condition of the operator for relaxing the operator,
   wherein said detection means comprises means for discriminating the mental condition in accordance with information representing the degree of concentration of the operator on work related to instructions given by the operator to said processing means.

8. An apparatus according to claim 7, wherein said discriminating means comprises means for discriminating pupil movement of the operator.

9. An apparatus accordng to claim 7, wherein said discriminating means comprises means for discriminating the frequency of input errors of the operator input into said apparatus for instructing said processing means.

10. An apparatus according to claim 7, wherein said output means comprises acoustic output means for outputting a speech message or a melody.

11. An apparatus according to claim 7, wherein said output means outputs image information.

12. An apparatus according to claim 7, wherein said output means comprises means for generating a message representing an inquiry to the operator.

13. An apparatus according to claim 7, wherein said output means comprises means for generating variable sound information in response to the mental condition of the operator.

14. An apparatus according to claim 7, further comprising:
   means for determining the time;
   power detecting means for detecting that said apparatus is supplied with power; and
   means for controlling said output means to output a timely message to the operator in response to the time determined by said determining means when said power detecting means detects that said apparatus is supplied with power.

15. An information apparatus comprising:
   processing means for performing various information processing operations in accordance with an instruction from an operator;
   detection means for detecting a mental condition of the operator during information processing operations performed by said processing means in accordance with an instruction from the operator by detecting the operation time of the operator; and
   output for outputting information corresponding to the detected mental condition of the operator for relaxing the operator.

16. An apparatus according to claim 15, wherein said output means comprises acoustic output means for outputting a speech message or a melody.

17. An apparatus according to claim 15, wherein said output means outputs image information.

18. An apparatus according to claim 15, wherein said output means comprises means for generating a message representing an inquiry to the operator.

19. An apparatus according to claim 15, wherein said output means comprises means for generating variable sound information in response to the mental condition of the operator.

20. An apparatus according to claim 15, further comprising:
   means for determining the time;
   power detecting means for detecting that said apparatus is supplied with power; and
   means for controlling said output means to output a timely message to the operator in response to the time determined by said determining means when said power detecting means detects that said apparatus is supplied with power.

21. An information processing apparatus comprising:
   storage means for storing personality information for each of a plurality of operators;
   selection means for selecting personality information for a given operator from the personality information for each of the plurality of operators stored in said storage means;
   detection means for detecting a mental condition of the given operator; and
   output means for outputting information corresponding to the mental condition of the given operator based on the personality information for the given operator for relaxing the given operator.

22. An apparatus according to claim 21, wherein said selection means selects the basic information in accordance with an identification number of the operator.

23. An apparatus according to claim 21, wherein said output means comprises acoustic output means for outputting a speech message or a melody.

24. An apparatus according to claim 21, wherein said output means outputs image output information comprising a character message or an image.

25. An apparatus according to claim 21, wherein said output means comprises means for generating a message representing an inquiry to the operator.

26. An apparatus according to claim 21, wherein said output means comprises means for generating variable sound information in response to the mental condition of the operator.

27. An apparatus according to claim 21, further comprising:
   means for determining the time;
   power detecting means for detecting that said apparatus is supplied with power; and means for controlling said output means to output a timely message to the operator in response to the time determined by said determining means when said power detecting means detects that said apparatus is supplied with power.

28. An information processing apparatus comprising:
storage means for storing preference information for each of a plurality of operators;
selection means for selecting the preference information for a given operator from the preference information for each of the plurality of operators stored in said storage means;
detection means for detecting a mental condition of the given operator; and
output means for outputting information corresponding to the mental condition of the given operator based on the preference information for the given operator for relaxing the given operator.

29. An apparatus according to claim 28, wherein said selection means selects the preference information in accordance with an identification number of the operator.

30. An apparatus according to claim 28, wherein said output means comprises acoustic output means for outputting a speech message or a melody.

31. An apparatus according to claim 28, wherein said output means outputs image information.

32. An apparatus according to claim 28, wherein said output means comprises means for generating a message representing an inquiry to the operator.

33. An apparatus according to claim 28, wherein said output means comprises means for generating variable sound information in response to the mental condition of the operator.

34. An apparatus according to claim 28, further comprising:
means for determining the time;
power detecting means for detecting that said apparatus is supplied with power; and
means for controlling said output means to output a timely message to the operator in response to the time determined by said determining means when said power detecting means detects that said apparatus is supplied with power.

35. An information processing apparatus comprising:
storage means for storing basic information for each of a plurality of operators;
selection means for selecting basic information for a given operator from the basic information for each of the plurality of operators stored in said storage means;
detection means for detecting a mental condition of the given operator by detecting information representative of the personality of the operator; and
output means for outputting information corresponding to the mental condition of the given operator based on the basic information for the given operator for relaxing the given operator.

36. An apparatus according to claim 35, wherein said selection means selects the basic information in accordance with an identification number of the operator.

37. An apparatus according to claim 35, wherein said output means comprises acoustic output means for outputting a speech message or a melody.

38. An apparatus according to claim 35, wherein said output means outputs image information.

39. An apparatus according to claim 35, wherein said output means comprises means for generating a message representing an inquiry to the operator.

40. An apparatus according to claim 35, wherein said output means comprises means for generating variable sound information in response to the mental condition of the operator.

41. An apparatus according to claim 35, further comprising:
means for determining the time;
power detecting means for detecting that said apparatus is supplied with power; and
means for controlling said output means to output a timely message to the operator in response to the time determined by said determining means when said power detecting means detects that said apparatus is supplied with power.

42. An information processing apparatus comprising:
storage means for storing basic information for each of a plurality of operators;
selection means for selecting basic information for a given operator from the basic information for each of the plurality of operators stored in said storage means;
detection means for detecting a mental condition of the given operator by detecting information representing the degree of concentration of the operator on work; and
output means for outputting information corresponding to the mental condition of the given operator based on the basic information for the given operator for relaxing the given operator.

43. An apparatus according to claim 42, wherein said information detection means comprises means for discriminating the pupil movement of the operator.

44. An apparatus according to claim 42, wherein the operator inputs information into said apparatus, wherein said information detection means comprises means for detecting the frequency of input errors of the operator.

45. An apparatus according to claim 42, wherein said selection means selects the basic information in accordance with an identification number of the operator.

46. An apparatus according to claim 42, wherein said output means comprises acoustic output means for outputting a speech message or a melody.

47. An apparatus according to claim 42, wherein said output means outputs image information.

48. An apparatus according to claim 42, wherein said output means comprises means for generating a message representing an inquiry to the operator.

49. An apparatus according to claim 42, wherein said output means comprises means for generating variable sound information in response to the mental condition of the operator.

50. An apparatus according to claim 42, further comprising:
means for determining the time;
power detecting means for detecting that said apparatus is supplied with power; and
means for controlling said output means to output a timely message to the operator in response to the time determined by said determining means when said power detecting means detects that said apparatus is supplied with power.

51. An information processing apparatus comprising:
storage means for storing basic information for each of a plurality of operators;

selection means for selecting basic information for a given operator from the basic information for each of the plurality of operators stored in said storage means;

detection means for detecting a mental condition of the given operator by detecting the operation time of the operator; and output means for outputting information corresponding to the mental condition of the given operator based on the basic information for the given operator for relaxing the given operator.

52. An apparatus according to claim 51, wherein said selection means selects the basic information in accordance with an identification number of the operator.

53. An apparatus according to claim 51, wherein said output means comprises acoustic output means for outputting a speech message or a melody.

54. An apparatus according to claim 51, wherein said output means outputs image information.

55. An apparatus according to claim 51, wherein said output means comprises means for generating a message representing an inquiry to the operator.

56. An apparatus according to claim 51, wherein said output means comprises means for generating variable sound information in response to the mental condition of the operator.

57. An apparatus according to claim 51, further comprising:

means for deriving time information;

power detecting means for detecting an event that said apparatus is placed in condition of power on; and means for controlling said output means to tell a timely message to the operator in response to the time information derived by said deriving means when the event is detected by said power detecting means.

58. An information apparatus comprising:

an office automation device adapted to perform various information processing operations in accordance with instructions from an operator;

a bioinformation sensor, including means for detecting the operator's mental condition by observing the operator's operating time in operating said office automation device; said bioinformation sensor generating information representative of the operator's mental condition; and a display device connected to said sensor to receive the information from said sensor, wherein said display device displays information corresponding to the sensed mental condition of the operator, as represented by the information received by said display device from said sensor.

59. An apparatus according to claim 58, wherein said display device displays image information.

60. An apparatus according to claim 58, wherein said display device comprises means for generating a message representing an inquiry to the operator.

61. An apparatus according to claim 58 further comprising:

means for determining the time;

power detecting means for detecting that said apparatus is supplied with power; and means for controlling said display device to display a timely message to the operator in response to the time determined by said determining means when said power detecting means detects that said apparatus is supplied with power.

62. An apparatus according to claim 58, wherein said bioinformation sensor comprises a far-infrared sensor.

63. An apparatus according to claim 58, wherein said bioinformation sensor observes the operating time by detecting movement of a pupil of the operator.

64. An apparatus according to claim 58, wherein said bioinformation sensor is mounted on a key arranged in said office automation device.

65. An apparatus according to claim 58, further comprising means for generating a sound message including music, wherein said sound generating means generates a sound suitable for the sensed mental condition when said display device displays the information.

* * * * *

UNITED STATES PATENT AND TRADEMARK OFFICE
CERTIFICATE OF CORRECTION

PATENT NO. : 4,894,777

DATED : January 16, 1990

INVENTOR(S) : Hirokazu Negishi, et al.

It is certified that error appears in the above-identified patent and that said Letters Patent is hereby corrected as shown below:

Title page:

At [75] Inventors:

"Hirokazu Negishi, Epsom Survey," should read
--Hirokazu Negishi, Epsom Surrey,--

COLUMN 1

Line 53, "devices)" should read --device)--.
Line 60, "apparatus" should read -- apparatuses--.
Line 64, "user" should read --user- --.
Line 66, "object." should read --object--.
Line 67, "man" should read --man.--.

COLUMN 2

Line 2, "being" should read --being made--.

COLUMN 3

Line 41, "and" should read --and merely--.

COLUMN 4

Line 61, "the should be deleted.

COLUMN 6

Line 31, "confort" should read --comfort--.

UNITED STATES PATENT AND TRADEMARK OFFICE
CERTIFICATE OF CORRECTION

PATENT NO. : 4,894,777

DATED : January 16, 1990

INVENTOR(S) : Hirokazu Negishi, et al.

It is certified that error appears in the above-identified patent and that said Letters Patent is hereby corrected as shown below:

COLUMN 12

Line 18, "claim 58" should read --claim 58,--.

Signed and Sealed this

Ninth Day of February, 1993

Attest:

STEPHEN G. KUNIN

Attesting Officer

Acting Commissioner of Patents and Trademarks